(12) United States Patent
Conley

(10) Patent No.: US 11,918,264 B2
(45) Date of Patent: Mar. 5, 2024

(54) HEADLESS COMPRESSION SCREW HAVING AN ATTACHMENT MECHANISM

(71) Applicant: Acumed LLC, Hillsboro, OR (US)

(72) Inventor: Brian Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 359 days.

(21) Appl. No.: 17/470,449

(22) Filed: Sep. 9, 2021

(65) Prior Publication Data
US 2022/0079642 A1   Mar. 17, 2022

Related U.S. Application Data

(60) Provisional application No. 63/079,237, filed on Sep. 16, 2020.

(51) Int. Cl.
| | | |
|---|---|---|
| A61B 17/86 | (2006.01) | |
| A61B 17/04 | (2006.01) | |
| A61B 17/68 | (2006.01) | |

(52) U.S. Cl.
CPC ........ *A61B 17/864* (2013.01); *A61B 17/0401* (2013.01); *A61B 17/8645* (2013.01); *A61B 2017/044* (2013.01); *A61B 2017/681* (2013.01)

(58) Field of Classification Search
CPC .................................................. A61B 17/864
See application file for complete search history.

(56) References Cited

U.S. PATENT DOCUMENTS

| | | | | |
|---|---|---|---|---|
| 4,175,555 | A * | 11/1979 | Herbert ................ | A61B 17/863 606/304 |
| 10,405,903 | B1 * | 9/2019 | Biesinger ............. | A61B 17/866 |
| 2016/0287301 | A1 | 10/2016 | Mehl et al. | |
| 2016/0310127 | A1 | 10/2016 | Cavallazzi et al. | |
| 2018/0303529 | A1 * | 10/2018 | Zastrozna ............ | A61B 17/864 |
| 2019/0262047 | A1 * | 8/2019 | Sommers ........... | A61B 17/8635 |
| 2019/0262048 | A1 * | 8/2019 | Sutika .................. | A61B 17/864 |
| 2019/0336270 | A1 | 11/2019 | Dacosta et al. | |

(Continued)

FOREIGN PATENT DOCUMENTS

CN          207666676 U        7/2018

OTHER PUBLICATIONS

International Search Report corresponding to related International Patent Application No. PCT/US2021/049611 dated Dec. 10, 2021, 3 pages.

(Continued)

*Primary Examiner* — Christian A Sevilla
(74) *Attorney, Agent, or Firm* — K&L Gates LLP

(57) ABSTRACT

A cannulated headless compression screw is provided with an attachment mechanism that enables coupling various attachments to the headless compression screw. The headless compression screw includes a screw thread on its exterior that is adapted to effect compression between two bone fragments. For instance, the exterior screw thread may have a variable pitch formed to effect such compression. The interior of the headless compression screw's trailing end includes an interface that is adapted to engage with a driving instrument. A surgeon may drive the headless compression screw into bone via the driving instrument and then access the attachment mechanism to couple an attachment to the headless compression screw.

20 Claims, 8 Drawing Sheets

(56) References Cited

U.S. PATENT DOCUMENTS

2020/0146735 A1   5/2020   Pepper et al.

OTHER PUBLICATIONS

International Written Opinion corresponding to related International Patent Application No. PCT/US2021/049611 dated Dec. 10, 2021, 5 pages.
International Preliminary Report corresponding to related International Patent Application No. PCT/US2021/049611, dated Mar. 30, 2023, 8 pages.

* cited by examiner

HEADLESS COMPRESSION SCREW HAVING AN ATTACHMENT MECHANISM

PRIORITY CLAIM

The present application claims priority to and the benefit of U.S. Provisional Application 63/079,237, filed Sep. 16, 2020, the entirety of which is herein incorporated by reference.

BACKGROUND

To help heal bone fractures, it is desirable to compress the fractures so that the fractured bone surfaces are pressed against one another. Typically, bone screws have been used to draw the fractured bone surfaces together and thereby help the healing process. Some typical bone screws include a head connected to a threaded root portion. Such typical headed screws, however, may have a number of drawbacks including concentrated loads beneath the screw head and the screw head's protrusion away from the bone, particularly around articulating surfaces, once inserted.

Another potential drawback is a bone fragment nearest the screw head is held relative to the far bone fragment purely by compressive forces provided by the screw head. If the cortical bone layer directly under the screw head provides inadequate support either during insertion or subsequently, then compression is lost and the near bone fragment may be free to move relative to the trailing part (e.g., near the head) of the screw. Consequently, relative movement between the bone fragments may occur, which harms the healing process. In addition, a further drawback is bone resorption, which is a physiological response to localized pressure. Bone resorption may occur either directly under the screw head or at the fracture site. When resorption occurs, the screw may loosen which allows relative movement between the bone fragments to occur and harms the healing process.

Headless compression screws offer several advantages as compared to headed compression screws in various instances. Headless compression screws are installed completely within the two bone fragments thereby leaving no part to protrude away from the bone surface as compared to the protruding head of an installed headed screw, which may be beneficial in certain procedures. Additionally, headless compression screws effect and maintain compression between the bone fragments due to variable thread formation, and in no part by compressive forces provided by a head. Accordingly, headless compression screws do not produce the concentrated loads that headed screws produce as described above, which may be beneficial in certain procedures.

Additionally, in some instances, a surgical procedure may involve the installation of suture, anchors, plates, other implants, etc. along with a headed or headless compression screw. For example, a patient may have a soft tissue or ligament injury in addition to a bone fracture. Such a compound injury requires both a compression screw to draw the bone fragments together and suture to secure the injured soft tissue or ligament to bone. Typically, when using a headless compression screw to treat such compound injuries, a surgeon must install a headless compression screw and subsequently use suture to secure the soft tissue, either using a suture anchor into bone or performing other suture attachment techniques. Installing two or more components may contribute to longer surgical procedure times and lengthier patient recovery times.

Accordingly, there exists a need for a headless compression screw that solves the above drawbacks.

SUMMARY

The present disclosure provides new and innovative systems and methods for treating bone fractures with a headless compression screw, such as a compound injury having a bone fracture and a soft tissue or ligament injury. In an example, a system includes a headless compression screw and an attachment. The headless compression screw includes a hollow root portion having a leading end and a trailing end and an interior channel extending from the leading end to the trailing end. An exterior screw thread is formed on at least a portion of the exterior of the hollow root portion between the leading end and the trailing end. An interior screw thread is formed on the interior of the hollow root portion at its trailing end. A portion of the interior of the hollow root portion's trailing end is configured to engage with a driving instrument. The attachment includes a threaded portion configured to engage the hollow root portion's interior screw thread such that when engaged the attachment is coupled to the headless compression screw.

In another example, a system includes a headless compression screw and an attachment. The headless compression screw includes a hollow root portion having a leading end and a trailing end and an interior channel extending from the leading end to the trailing end. An exterior screw thread is formed on at least a portion of the exterior of the hollow root portion between the leading end and the trailing end. A notch is formed into the interior of the hollow root portion at its trailing end. A portion of the interior of the hollow root portion's trailing end is configured to engage with a driving instrument. The attachment includes a portion configured to engage the hollow root portion's notch such that when engaged the attachment is coupled to the headless compression screw.

In an example, a method for drawing two bones segments together and securing tissue to at least one of the two bone segments includes drilling a bone hole through the two bone segments. A headless compression screw is then inserted into the bone hole via a driving instrument such that the headless compression screw secures the two bones together. The headless compression screw includes a hollow root portion having a leading end and a trailing end and an interior channel extending from the leading end to the trailing end. An exterior screw thread is formed on at least a portion of the exterior of the hollow root portion between the leading end and the trailing end. An interior screw thread is formed on the interior of the hollow root portion at its trailing end. The driving instrument engages a portion of the interior of the hollow root portion's trailing end. After the headless compression screw is inserted into the bone hole, the method may include inserting a threaded portion of an attachment into the hollow root portion's interior screw thread such that the attachment couples to the headless compression screw. Suture may be secured to the attachment. Tissue may be secured to at least one of the two bone segments via the suture.

DETAILED DESCRIPTION

The present disclosure provides a cannulated headless compression screw with an attachment mechanism that enables coupling various attachments to the headless compression screw. The provided headless compression screw includes a leading end and a trailing end. The leading end is driven into bone. The interior of the headless compression screw's trailing end includes an interface that is adapted to engage with a driving instrument. For example, the trailing end may be adapted to engage with a hexagon-shaped driving instrument. A surgeon may therefore drive the headless compression screw into bone via the driving instrument. The headless compression screw includes a screw thread on its exterior that is adapted to effect compression between two bone fragments when the headless compression screw is installed across a fracture. For instance, the exterior screw thread may have a variable pitch formed to effect such compression.

The headless compression screw's attachment mechanism is within the interior of the headless compression screw. In some instances, the attachment mechanism may include an interior thread such that an attachment may be coupled to the headless compression screw by threaded engagement. In other instances, the attachment mechanism may include a notch such that an attachment may be coupled to the headless compression screw by snapping into or engaging with the notch. In some examples, the attachment mechanism may be closer to the leading end than the driver instrument interface. Such examples may help a surgeon engage a driving instrument with the headless compression screw's interface without interference from the attachment mechanism. For instance, once the surgeon installs the headless compression screw into bone and removes the driving instrument, the surgeon may then couple an attachment to the headless compression screw.

The attachment may be any suitable implant that adds utility to a surgical procedure utilizing the provided headless compression screw. For example, a patient may have a compound injury including a bone fracture and a soft tissue or ligament injury. A surgeon may install the provided compression screw across the fracture to help heal the bone fracture. Typically, to help heal the soft tissue or ligament injury, the surgeon may install a suture anchor into bone (e.g., one of the bone fragments of the fracture) so that the surgeon may secure the soft tissue or ligament to the bone with suture via the suture anchor. The provided headless compression screw, however, enables the surgeon to instead couple a suture anchor to the headless compression screw itself. By eliminating the need to install a separate suture anchor into bone, the provided headless compression screw helps contribute to shorter surgical procedure times and may aid in shorter patient recovery times. Other example attachments will be described in more detail below.

Figure 1A:
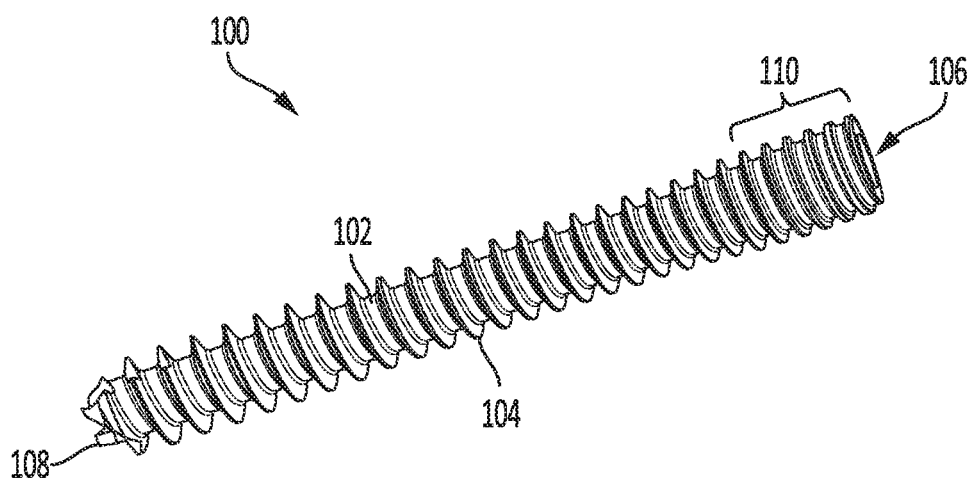
FIGS. 1A and 1B illustrate a perspective and cross-sectional view respectively of a headless compression screw having a threaded attachment insert, according to an aspect of the present disclosure.
Figure 1B:
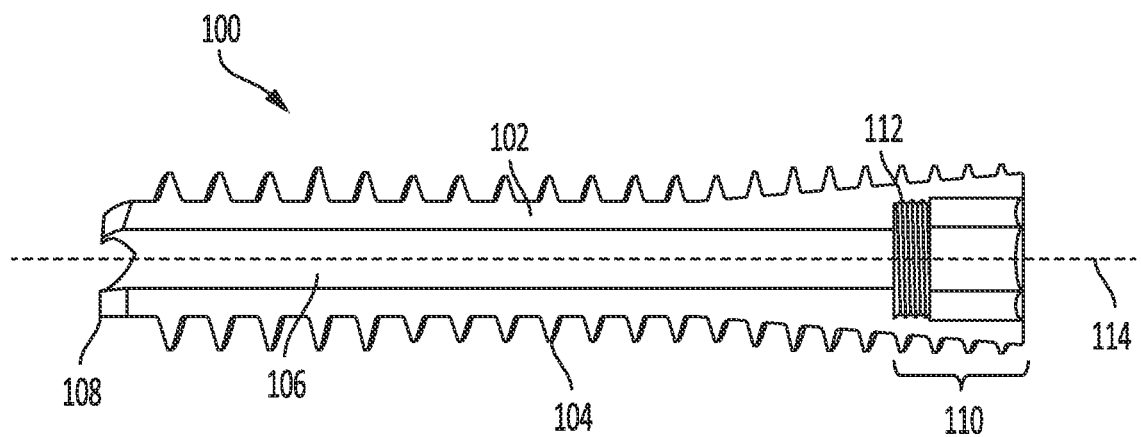

FIGS. 1A and 1B illustrate a perspective and cross-sectional view respectively of an example headless compression screw 100. The example headless compression screw 100 includes a root portion 102. The root portion 102 extends from a leading end 108 to a trailing end 110. The root portion 102 is cannulated or hollow such that it includes a channel 106 that extends from the leading end 108 to the trailing end 110. The channel 106 is configured such that the headless compression screw 100 may be positioned over a guide wire.

An exterior thread 104 is formed on at least a portion of the root portion 102 between the leading end 108 and the trailing end 110. For instance, the exterior thread 104 may be formed such that it is a continuous thread extending from the leading end 108 to the trailing end 110. In another instance, the exterior thread 104 may be that of a differential pitch or Herbert screw, as will be appreciated by one having skill in the art. The exterior thread 104 is particularly adapted to effect compression between two bone fragments as a surgeon drives the headless compression screw 100 into bone and across a fracture. For example, the pitch of the exterior thread 104 may be larger near the leading end 108 as compared to the trailing end 110. The pitch of the exterior thread 104 is measured between corresponding points on consecutive thread crests. In another example, the crest radius of the exterior thread 104 may be larger near the trailing end 110 as compared to the leading end 108. The crest radius of the exterior thread 104 is measured from a central axis 114 to an outermost point on the exterior thread 104. In at least one example, the exterior thread 104 may be formed with a variable pitch as described in U.S. Pat. No. 5,871,486, which is herein incorporated by reference.

Figure 2:
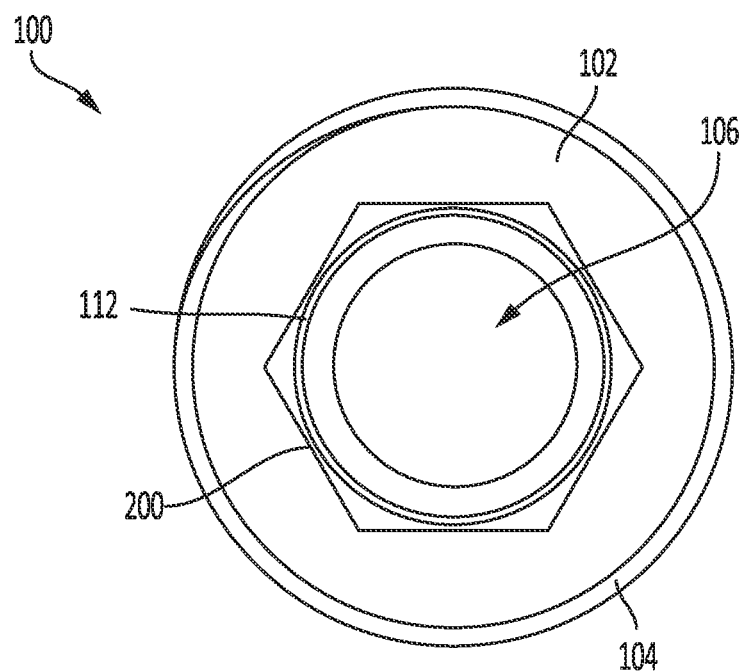
FIG. 2 illustrates a view along a long axis of the headless compression screw shown in FIGS. 1A and 1B, according to an aspect of the present disclosure.

The interior of the trailing end 110 of the headless compression screw 100 may be configured to include a driver interface (e.g., driver interface 200 in FIG. 2). A surgeon may position a driving instrument within the driver interface to engage the driving instrument to the headless compression screw 100 and drive the headless compression screw 100 into bone. When engaged, the driving instrument is positioned and maintained fully within the channel 106 of the headless compression screw 100. Such a configuration that maintains the driving instrument fully within the channel 106 helps maximize engagement between the driving instrument and the headless compression screw 100. It also may help limit the driving instrument's contact with the bone hole during insertion of the headless compression screw 100. The leading end 108 of the headless compression screw 100 is configured to drive into bone to advance the headless compression screw 100 through bone.

The interior of the trailing end 110 of the example headless compression screw 100 also includes a threaded attachment mechanism 112. The threaded attachment mechanism 112 enables a surgeon to couple an attachment to the headless compression screw 100 by threaded engagement. The threaded attachment mechanism 112 may be closer to the leading end 108 than the driver interface, as illustrated. Such positioning enables a driving instrument to engage the headless compression screw 100 without interference from the threaded attachment mechanism 112. Once a surgeon drives the headless compression screw 100 into bone and removes the driving instrument, the threaded attachment mechanism 112 may be accessed so that a surgeon may couple an attachment to the headless compression screw 100. Additionally, if an attachment is not needed, a surgeon may simply not add an attachment. The threaded attachment mechanism 112 is within the interior of the headless compression screw 100 and does not affect insertion of the headless compression screw 100. Further, the headless compression screw 100 provides the same fracture compression benefits with or without an attachment added. Thus, an attachment is an optional add-on to provide an additional feature.

In some aspects, the threaded attachment mechanism 112 is threaded opposite of the exterior thread 104. Stated differently, the exterior thread 104 may be configured such that threaded engagement is advanced clockwise whereas the threaded attachment mechanism 112 may be configured such that threaded engagement is advanced counter-clockwise, or vice versa. In such aspects, a surgeon may thread a driving instrument into the threaded attachment mechanism 112 to remove the headless compression screw 100 from bone. This feature is beneficial if the driver interface becomes damaged and therefore cannot be used to remove the headless compression screw 100 from bone.

Figure 1C:
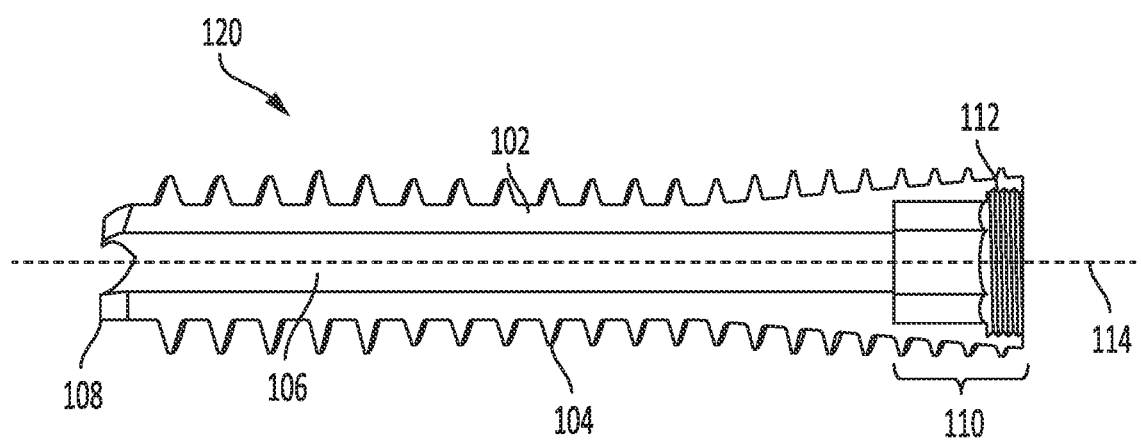
FIG. 1C illustrates a cross-sectional view of a headless compression screw having a driver interface oriented opposite of a threaded attachment insert as compared to the headless compression screw of FIGS. 1A and 1B.

FIG. 1C illustrates a cross-sectional view of an example headless compression screw 120. The headless compression screw 120 may be similar to the headless compression screw 100, except that the driver interface (e.g., driver interface 200 in FIG. 2) is oriented opposite of the threaded attachment mechanism 112. As shown, in such an example, the threaded attachment mechanism 112 is wider than the driver interface so that a drive mechanism fits within the minor diameter of the threads in the threaded attachment mechanism 112. The wider threaded attachment mechanism 112 enables the drive mechanism to engage the headless compression screw 120 without interference from the threaded attachment mechanism 112.

FIG. 2 illustrates a view of the trailing end 110 along a long axis of the headless compression screw 100 showing an example driver interface 200. As illustrated, the driver interface 200 may have a larger cross sectional area than the threaded mechanism 112 and the remaining portion of the channel 106. Such a configuration prevents a driving instrument from being inserted past the threaded attachment mechanism 112 and into the remaining portion of the channel 106. The example driver interface 200 is adapted for use with a hexagon-shaped driving instrument. In other examples, the driver interface 200 may be adapted for use with driving instruments having other shapes, such as hexalobe, square, Phillips, Pozidriv, Torx, Security T, etc.

The headless compression screw 100 may be constructed of any suitable biocompatible material. For example, stainless steel, a cobalt-chromium alloy, titanium, a titanium alloy, magnesium, or polyether ether ketone (PEEK) are suitable biocompatible materials.

Figure 3A:
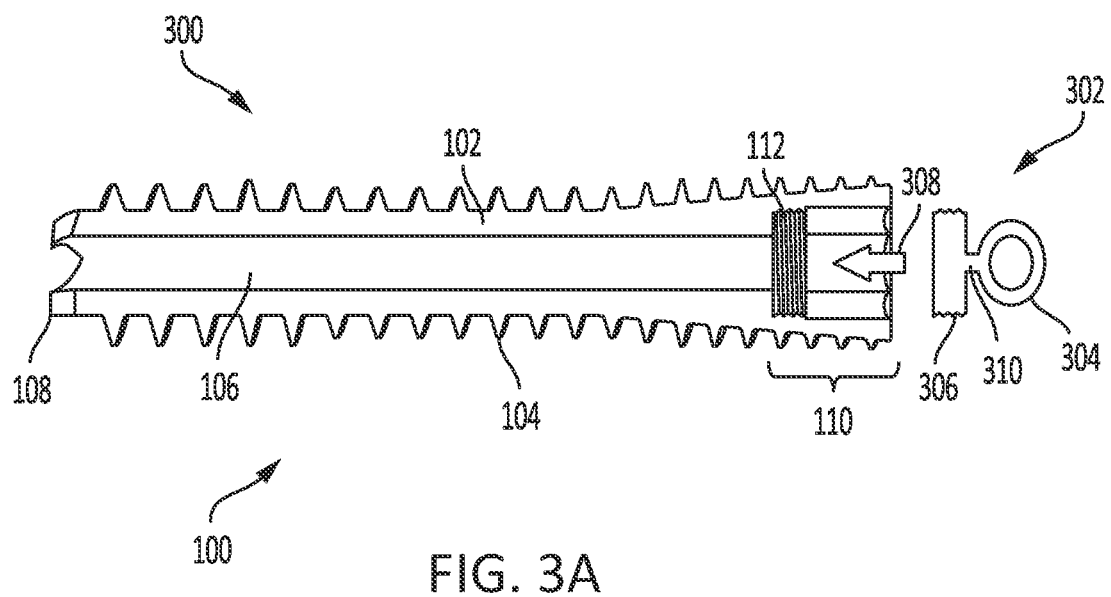
FIGS. 3A and 3B illustrate cross sectional views of a system including a headless compression screw and a suture anchor attachment having an eyelet, according to an aspect of the present disclosure.
Figure 3B:
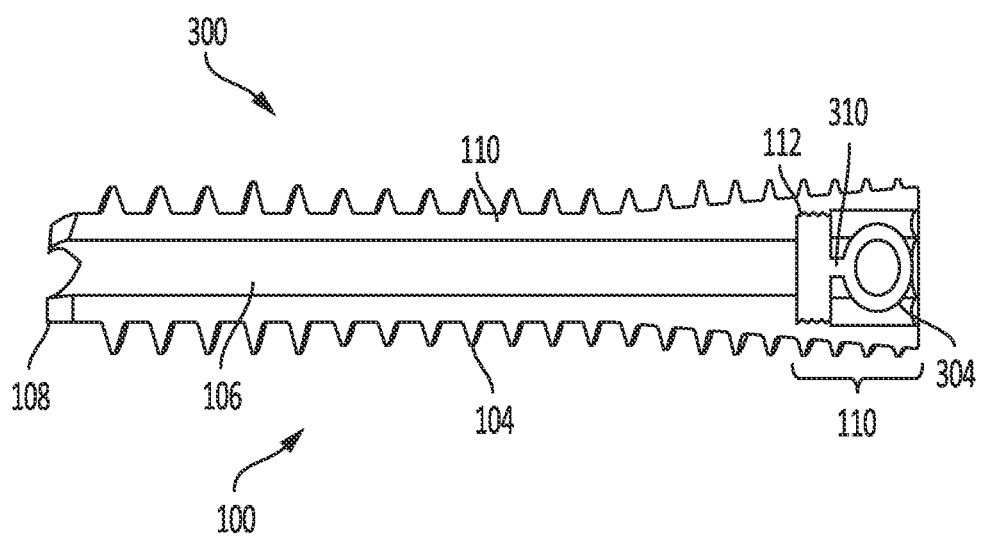

One example of an attachment that may be coupled to the headless compression screw 100 is a suture anchor. FIGS. 3A and 3B illustrate cross sectional views of an example system 300 that includes the headless compression screw 100 and an example suture anchor attachment 302. The suture anchor attachment 302 may attach to the headless compression screw 100 and couple suture to the headless compression screw 100. In some instances, the example suture anchor attachment 302 may have a fully closed eyelet 304 through which suture may be passed, such as the illustrated example. In other instances, the suture anchor attachment 302 may have an eyelet 304 that is not fully closed such that it is a hook that secures suture.

The suture anchor attachment 302 may include a threaded portion 306. The eyelet 304 may be connected to the threaded portion 306 by an arm 310. The threaded portion 306 is adapted to engage the threaded attachment mechanism 112. A surgeon may translate the suture anchor attachment 302 in the direction of the arrow 308 as shown in FIG. 3A and rotate it to engage the suture anchor attachment 302 with the threaded attachment mechanism 112, thereby coupling the suture anchor attachment 302 to the headless compression screw 100 as shown in FIG. 3B. In the illustrated example, the eyelet 304 is fully within the channel 106 when the threaded portion 306 of the suture anchor attachment 302 is fully engaged with the threaded attachment mechanism 112. In other examples, the arm 310 may be longer such that a portion or all of the eyelet 304 extends outside of the channel 106.

In an example, as described above, a surgeon may install the headless compression screw 100 across a fracture to help the fracture heal and may couple suture to the suture anchor attachment 302 to secure an injured soft tissue or ligament to one of the bone fragments, which helps the soft tissue or ligament heal. The suture may be passed through the eyelet 304 before the suture anchor attachment 302 is coupled to the headless compression screw 100 or after the suture anchor attachment 302 is coupled to the headless compression screw 100. The example system 300 including a headless compression screw 100 and a coupled suture anchor attachment 302 may be used with a standard suture technique or a knotless suture construct.

Figure 4A:
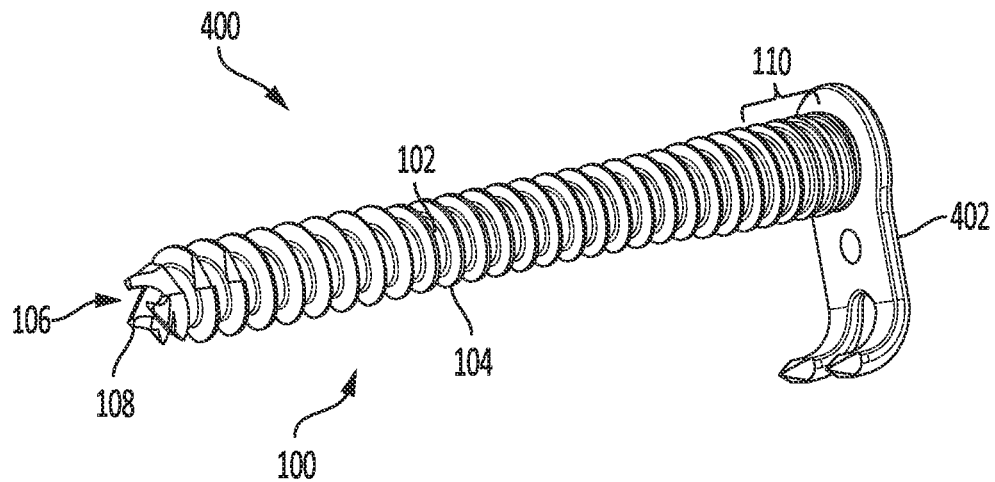
FIG. 4A illustrates a system including a headless compression screw and a one-sided avulsion hook plate, according to an aspect of the present disclosure.

Another example of an attachment that may be coupled to the headless compression screw 100 is a surgical plate. For example, the surgical plate may be an avulsion hook plate, though other suitable surgical plates may be coupled to the headless compression screw 100, such as a buttress plate, small fragment plates, pre-contoured bone plates, one-third tubular plate, or t-plates. Avulsion hook plates are typically used to treat an avulsion fracture, which is an injury to the bone in a location where a tendon or ligament attaches to the bone. When an avulsion fracture occurs, the tendon or ligament pulls a fragment of the bone away from the main part of the bone. An avulsion hook plate may be used to secure the bone fragment to the main part of the bone. Typically, an avulsion hook plate is coupled to the head of a screw that is installed in the main part of the bone. FIG. 4A illustrates a perspective view of an example system 400 that includes the headless compression screw 100 and a one-sided avulsion hook plate attachment 402. In some instances, the one-sided avulsion hook plate attachment 402 may include an opening though which a screw passes to couple the one-sided avulsion hook plate attachment 402 to the headless compression screw 100 (e.g., see the system 410 in FIG. 4B having a screw 414). In other instances, the one-sided avulsion hook plate attachment 402 includes a threaded part (not illustrated) that is engaged with the threaded attachment mechanism 112 (not illustrated) to couple the one-sided avulsion hook plate attachment 402 to the headless compression screw 100. The example system 400 enables a surgeon to treat a bone fracture as well as an avulsion fracture with a single tool. While the one-sided avulsion hook plate attachment 402 protrudes from a bone surface when coupled to an installed headless compression screw 100, the system 400 provides the other benefits of a headless compression screw described above.

Figure 4B:
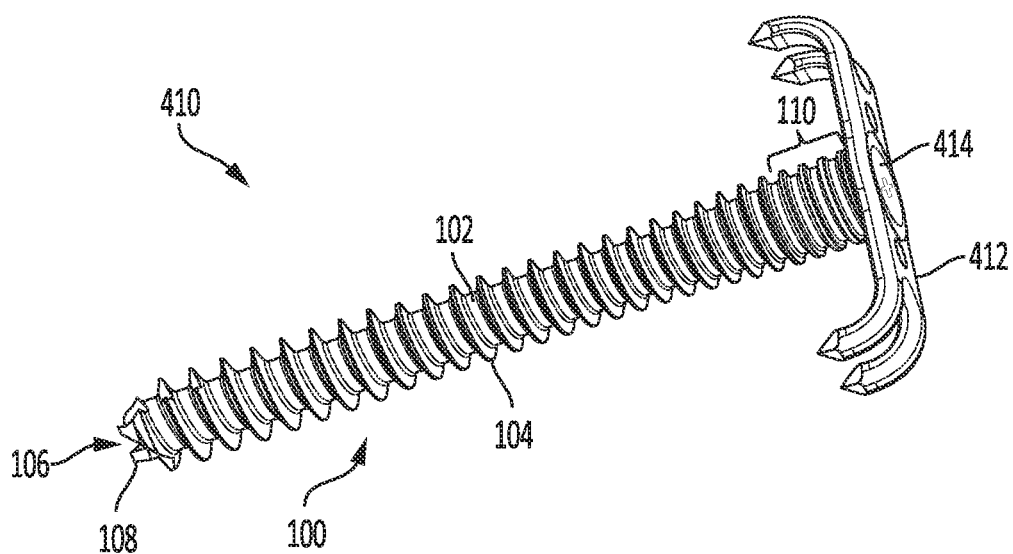
FIG. 4B illustrates a system including a headless compression screw and a two-sided avulsion hook plate, according to an aspect of the present disclosure.

FIG. 4B illustrates an example system 410 that includes the headless compression screw 100 and a two-sided avulsion hook plate attachment 412. In some instances, the two-sided avulsion hook plate attachment 412 may include an opening though which a screw 414 passes to couple the two-sided avulsion hook plate attachment 412 to the headless compression screw 100. The screw 414 engages the threaded attachment mechanism 112 (not illustrated). In other instances, the two-sided avulsion hook plate attachment 412 may include a threaded part that is engaged with the threaded attachment mechanism 112 (not illustrated) to couple the two-sided avulsion hook plate attachment 412 to the headless compression screw 100. The example system 410 enables a surgeon to treat complex fractures around an entry site for the headless compression screw 100 using a single tool. For example, the system 410 may enable a surgeon to treat a bone fracture as well as two separate avulsion fractures with a single tool. While the two-sided avulsion hook plate attachment 412 protrudes from a bone surface when coupled to an installed headless compression screw 100, the system 410 provides the other benefits of a headless compression screw described above.

It should be appreciated that the one-sided and two-sided avulsion hook plate attachments 402 and 412 are illustrated merely as example plates. The aspects described in connection with the one-sided and two-sided avulsion hook plate attachments 402 and 412 may be applied to other suitable surgical plates. For example, other suitable surgical plates may include buttress plates, small fragment plates, pre-contoured bone plates, one-third tubular plate, or t-plates.

Figure 5A:
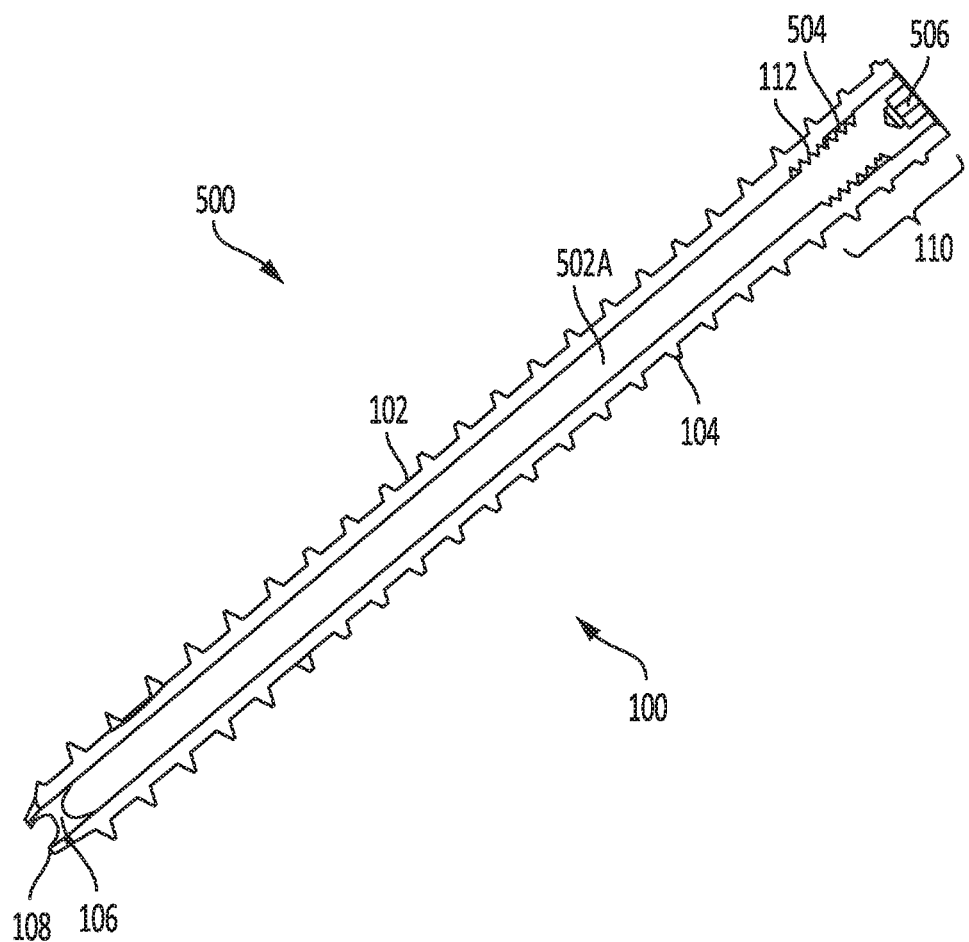
FIG. 5A illustrates a cross sectional view of a system including a headless compression screw and a solid core attachment, according to an aspect of the present disclosure.

A further example of an attachment that may be coupled to the headless compression screw 100 is a solid core. FIG. 5A illustrates a cross sectional view of an example system 500 that includes the headless compression screw 100 and a solid core attachment 502A. The solid core attachment 502A reinforces the cannulated headless compression screw 100 to increase the strength of the headless compression screw 100. For instance, the strength of the cannulated headless compression screw 100 may be increased to a strength comparable to a solid core compression screw. The solid core attachment 502A is configured to shape fit within the channel 106. Stated differently, there is very little to no space between the surface of the solid core attachment 502A and the interior surface of the headless compression screw 100 within the channel 106. The solid core attachment 502A may fill the entire length of the channel 106 or a portion of it. For example, the solid core attachment 502A may fill a substantial portion of the length of the channel 106 as illustrated. The solid core attachment 502A includes a threaded portion 504 such that the threaded portion 504 engages the threaded attachment mechanism 112 to couple the solid core attachment 502A to the headless compression screw 100.

The solid core attachment 502A may include a driver interface 506 adapted to engage with a driving instrument. In some aspects, the solid core attachment 502A may be coupled to the headless compression screw 100 prior to a surgeon installing the headless compression screw 100. The surgeon may then install the headless compression screw 100 into bone via engaging a driving instrument with the driver interface 506. In other aspects, the solid core attachment 502A may be coupled to the headless compression screw 100 after the surgeon installs the headless compression screw 100 into bone.

In some aspects, the solid core attachment 502A may be the same material as the headless compression screw 100. In other aspects, the solid core attachment 502A may be a different material than the headless compression screw 100. For example, the headless compression screw 100 may be constructed of titanium while the solid core attachment 502A is constructed of a cobalt-chromium alloy.

Figure 5B:
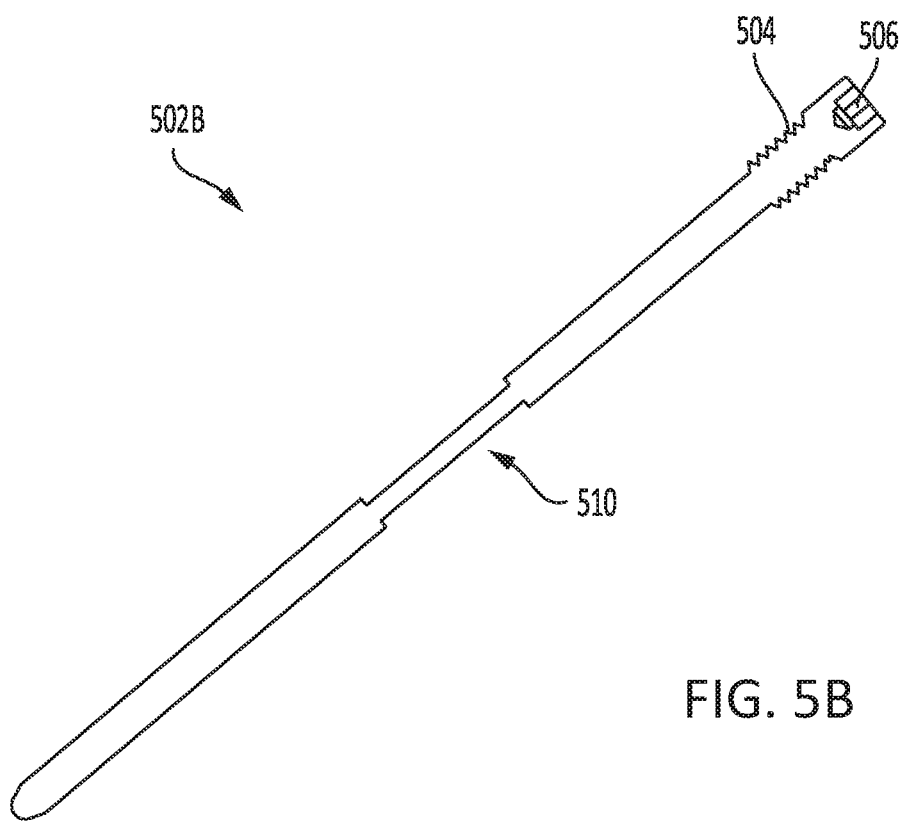
FIG. 5B illustrates a cross sectional view of a solid core attachment having a reduced section, according to an aspect of the present disclosure.
Figure 5C:
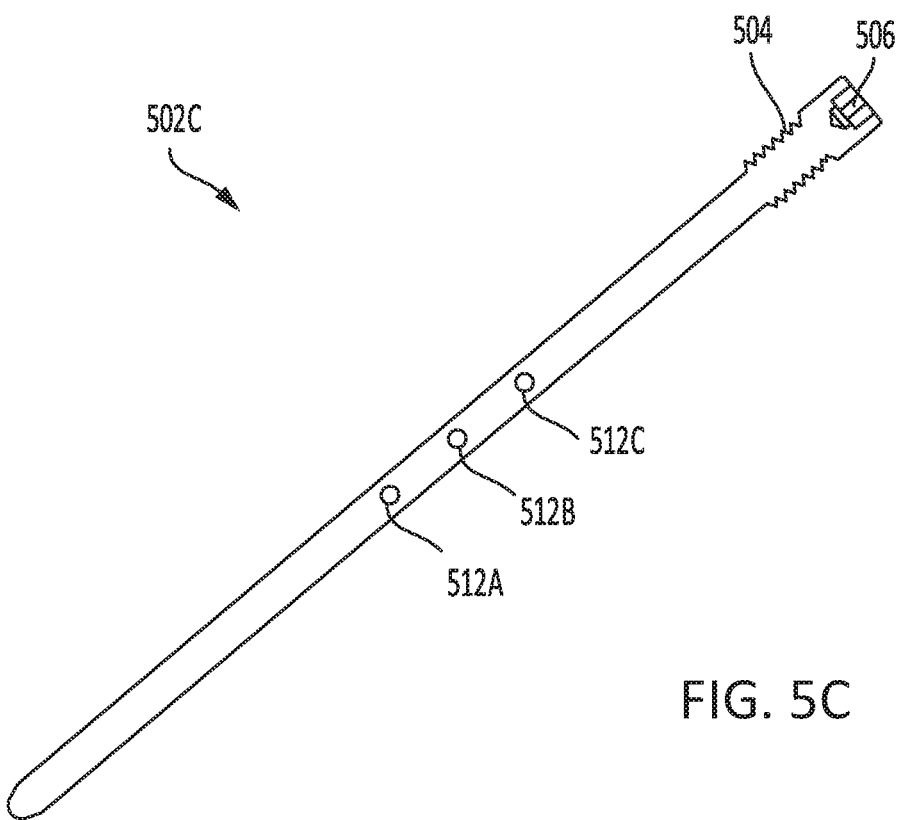
FIG. 5C illustrates a cross sectional view of a solid core attachment having multiple holes, according to an aspect of the present disclosure.

Additionally, in some aspects, the solid core attachment may be constructed such that its stiffness or strength is reduced as compared to the uniformly solid example solid core attachment 502A illustrated in FIG. 5A. For instance, FIG. 5B illustrates a solid core attachment 502B having a reduced portion 510. The reduction of material at the reduced portion 510 reduces the stiffness or strength of the solid core attachment 502B as compared to the solid core attachment 502A. In another instance, FIG. 5C illustrates a solid core attachment 502C having multiple holes 512A, 512B, 512C. The reduction of material by the holes 512A, 512B, 512C reduces the stiffness or strength of the solid core attachment 502C as compared to the solid core attachment 502A. The solid core attachment 502C may have any suitable quantity or shape of holes 512A, 512B, 512C. Various configurations may enable varying levels of stiffness or strength of the solid core attachment 502A, 502B, 502C. A surgeon may choose a solid core attachment 502A, 502B, 502C that has a desired level of stiffness or strength for a given procedure.

Figure 6:
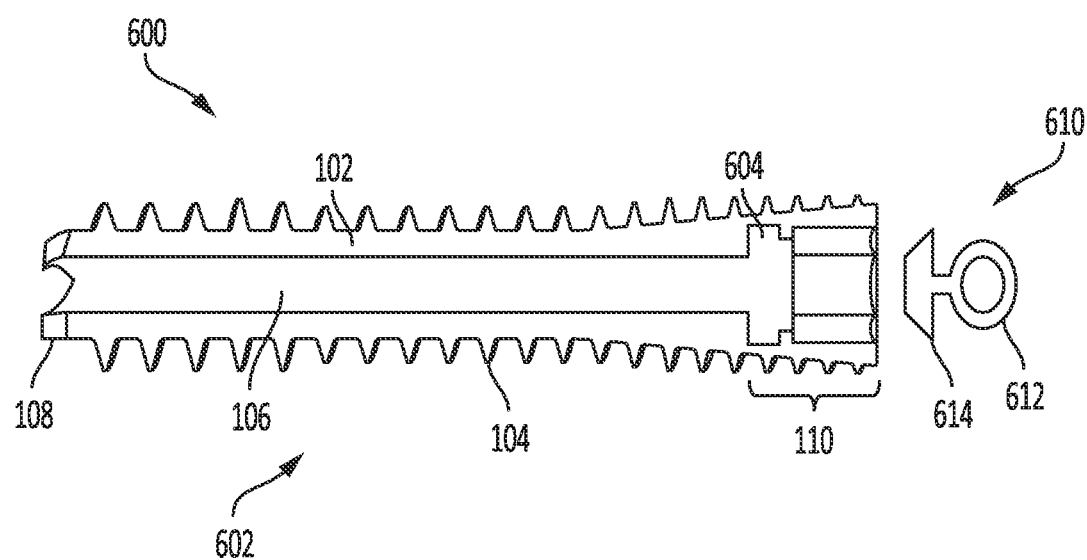
FIG. 6 illustrates a system including a headless compression screw having a snap attachment insert and a suture anchor attachment having an eyelet, according to an aspect of the present disclosure.

While the preceding examples of the provided headless compression screw are described as having a threaded attachment mechanism, other adaptations of the attachment mechanism are contemplated for coupling an attachment to the headless compression screw. For example, FIG. 6 illustrates a system 600 including an example headless compression screw 602 having a snap attachment mechanism 604. The system 600 also includes an example suture anchor attachment 610. The snap attachment mechanism 604 includes a notch formed into the interior surface of the headless compression screw 602. The suture anchor attachment 610 includes a snap portion 614. The snap portion 614 is configured to deform such that it snaps into the notch, thereby coupling the suture anchor attachment 610 to the headless compression screw 100. The suture anchor attachment 610 may have a fully closed eyelet 612, such as the illustrated example. In other instances, the suture anchor attachment 610 may have an eyelet 612 that is not fully closed such that it is a hook that secures suture. It should be understood that any of the attachments described herein may be configured with a snap portion instead of a threaded portion such that they engage with a provided headless compression screw having a snap attachment mechanism.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A system comprising:
a headless compression screw including:
a hollow root portion having a leading end and a trailing end and an interior channel extending from the leading end to the trailing end,
an exterior screw thread formed on at least a portion of an exterior of the hollow root portion between the leading end and the trailing end, and
an interior screw thread formed on the interior channel of the hollow root portion at its trailing end,
wherein a portion of the trailing end of the interior of the hollow root portion is configured to engage with a driving instrument; and
an attachment including a threaded portion configured to engage the interior screw thread of the hollow root portion such that when engaged the attachment is coupled to the headless compression screw.

2. The system of claim 1, wherein a pitch of the exterior screw thread, measured between corresponding points on consecutive thread crests, is larger near the leading end as compared to the trailing end.

3. The system of claim 1, wherein a crest radius of the exterior screw thread, measured from a central axis extending between the leading and trailing ends to an outermost point on the exterior screw thread, is larger near the trailing end as compared to the leading end.

4. The system of claim 1, wherein the exterior screw thread is threaded opposite of the interior screw thread.

5. The system of claim 1, wherein the attachment is adapted to secure suture to the attachment.

6. The system of claim 5, wherein the attachment includes a fully closed eyelet.

7. The system of claim 6, wherein the attachment is fully within the interior channel when coupled to the headless compression screw.

8. The system of claim 6, wherein the attachment extends outside of the interior channel when coupled to the headless compression screw.

9. The system of claim 1, wherein the attachment is a solid core.

10. The system of claim 9, wherein the solid core fills a substantial amount of the interior channel.

11. The system of claim 1, wherein the attachment is a surgical plate.

12. The system of claim 11, wherein the surgical plate is a one-sided avulsion hook plate.

13. The system of claim 11, wherein the surgical plate is a two-sided avulsion hook plate.

14. A system comprising:
a headless compression screw including:
a hollow root portion having a leading end and a trailing end and an interior channel extending from the leading end to the trailing end,
an exterior screw thread formed on at least a portion of an exterior of the hollow root portion between the leading end and the trailing end, and
a notch formed into the interior channel of the hollow root portion at its trailing end,
wherein a portion of the interior channel of the trailing end of the hollow root portion is configured to engage with a driving instrument; and
an attachment including a portion configured to engage the notch of the hollow root portion such that when engaged the attachment is coupled to the headless compression screw.

15. The headless compression screw of claim 14, wherein the interior channel is configured such that a guide wire may be positioned through the interior channel.

16. The headless compression screw of claim 14, wherein the notch is closer to the leading end than the portion of the trailing end configured to engage with the driving instrument.

17. The headless compression screw of claim 14, wherein the exterior screw thread is formed on the exterior of the hollow root portion so that it extends continuously from the leading end to the trailing end.

18. The headless compression screw of claim 14, wherein the headless compression screw is a Herbert-style headless compression screw.

19. A method for drawing two bone segments together and securing tissue to at least one of the two bone segments, the method comprising:
drilling a bone hole through the two bone segments;
inserting a headless compression screw into the bone hole via a driving instrument such that the headless compression screw secures the two bone segments together, wherein the headless compression screw includes:
a hollow root portion having a leading end and a trailing end and an interior channel extending from the leading end to the trailing end,
an exterior screw thread formed on at least a portion of an exterior of the hollow root portion between the leading end and the trailing end, and
a coupling portion formed on the interior channel of the trailing end of the hollow root portion,
wherein the driving instrument engages a portion of the interior of the trailing end of the hollow root portion;
inserting a portion of an attachment into the coupling portion of the hollow root portion after the headless compression screw is inserted into the bone hole such that the attachment couples to the headless compression screw;
securing suture to the attachment; and
securing tissue to at least one of the two bone segments via the suture.

20. The method of claim 19, wherein the headless compression screw is inserted into the bone hole over a guide wire.

* * * * *